Dec. 18, 1951 D. A. MOORE Plant Pat. 1,053
APRICOT TREE
Filed Sept. 29, 1947 2 SHEETS—SHEET 1
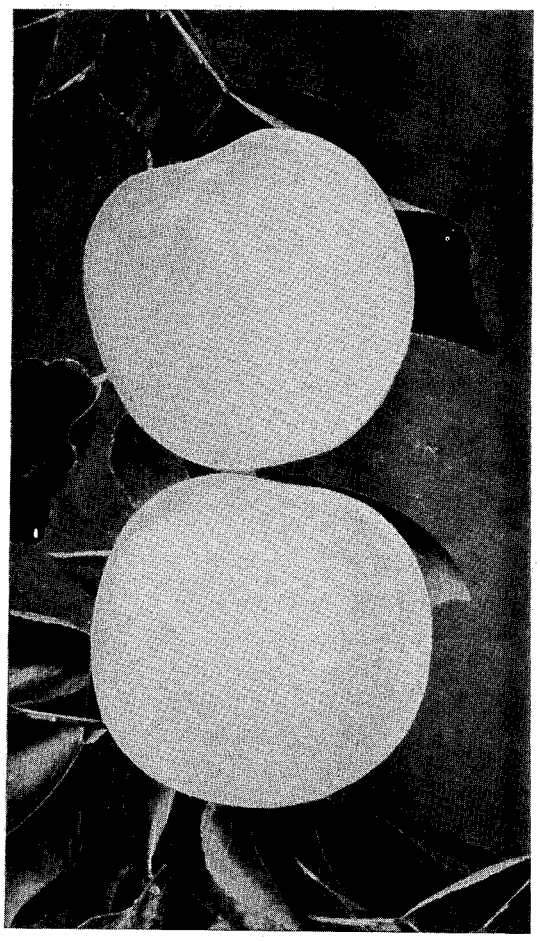
Inventor:
D. A. Moore
By: Robert Cobb
Attorneys.

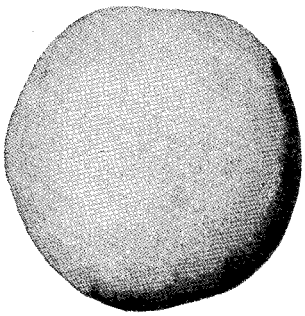
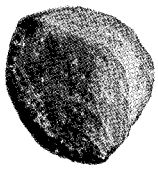
Inventor.
D. A. Moore
By: Robbins Cobb
Attorneys.

Patented Dec. 18, 1951 Plant Pat. 1,053

UNITED STATES PATENT OFFICE 1,053

APRICOT TREE

David A. Moore, Grand Junction, Colo., assignor to Inter-State Nurseries, Hamburg, Iowa, a partnership Application September 29, 1947, Serial No. 776,655

1 Claim. (Cl. 47—62)

The present discovery relates to a new and distinct variety of apricot tree, originally discovered by me in my cultivated orchard as a seedling which, since its discovery, has been characterized by its great vigor, continuous and consistent bearing year after year of high quality fruit of unusually large size, good flavor, and unusual shape and particularly suited for shipping purposes because of such shape.

While I am unable to state the parentage of this new variety with certainty, it evidently originated as a mutant to which my attention was attracted at first by its exceptional vigor and extra large leaves which distinguished it from all other varieties then being grown in my orchard.

The new variety has shown strong and healthy growing vigor by its prolific bearing habit when other varieties growing under comparable conditions failed to produce normally or otherwise. It is quite generally known that apricots picked green do not develop much of a good or outstanding flavor on ripening, but one of the most important characteristics of this new variety is that fruit packed green has a delicious flavor when ripe. This may be accounted for, at least in part, by its higher sugar content than any other apricot variety of which I am aware.

Even when the fruit is picked hard ripe, it stands shipping better than other varieties because of the firmness of the flesh, and another outstanding characteristic, namely, its substantially rectangular contour. The corners are not nearly as rounded as other fruit of oblong shape and this fact obviously facilitates the packing and enhances carrying or keeping qualities of this variety, in conjunction with possibility of picking it green up to hard ripe for transportation purposes.

The nearest variety to this new one, if it can be so compared, is probably one known as "Moorpark," (unpatented) but it takes little comparison to show the improvement over this last-named variety, particularly in its superiority in size, and in quality and productiveness.

By actual test, ripe specimens of the "Moorpark" variety showed a maximum sucrose content of 15.8% and a minimum of 9.6%, with an average of 13.1%, while corresponding specimens of this new variety taken from top of tree —tree ripe, showed a maximum in sucrose of 16.8% and an average of 15.6%; and tree run (young trees) specimens showed a maximum of 17.1%, a minimum of 11.0, with an average of 14.2%.

Asexual reproduction shows that these characteristics hold true through succeeding generations.

In the drawing are shown typical specimens of the fruit and one of the stones of this new variety.

The following is a detailed description of the new variety, color terminology being in accordance with Ridgway's Color Standard.

The specimens described were grown near Grand Junction, Colorado.

Dates of first and last picking, July 1–July 11.

*Tree*

Large; vigorous; spreading; open; round-topped; hardy; very productive; regular bearer.

Trunk: Stocky; medium smooth.

Branches: Stocky; smooth; glossy. *Color*—Claret Brown Plate 1, with small white spots. Lenticels—few; small.

Leaves: Length, 3"; width, 3½". Large; cordate; acutely pointed; thick.

*Color.*—Mature—dull dark Yellow Green, Plate 32. Young—Cress Green, Plate 31.

*Margin.*—Finely serrate.

*Petiole.*—Long; thick.

*Glands.*—Average number—four. Small globose; green. Position—double row, towards base of leaf.

*Stipules.*—None.

Flower buds: Hardy; medium size; medium length; plump; rounded; appressed very close to stem; smooth.

Flowers:

Dates first and full bloom—April 15th–April 17th, continuing to set new blooms over a period of about ten days. The date of commencement of bloom of the new variety is about the same as that of "Moorpark" and other standard varieties, but blooming of the new variety extends over a much longer period. Due to this long period of blossoming, the danger of killing by frost is minimized. Early; large; white tinged pink, fading white.

*Fruit*

Maturity when described: Ripe. Date—July 7th.
Size: Uniform; large. Diameter, axial, 2''; transverse in suture plane, 2⅜''; transverse at right angles to suture plane, 1¾''.
Form: Uniform; symmetrical; oblong; compressed laterally.
*Suture.*—Distinct; shallow; extends from base to apex but discontinuous at apex over entire circumference; has no depression beyond pistil point.
*Cavity.*—Abrupt; elongated in suture plane with suture showing on one side. Depth, 3/16'' to ¼''; breadth, ¼''; marking, none.
*Base.*—Oblique.
*Apex.*—Short and rounded. Pistil point—very inconspicuous at end of suture.
*Stem.*—Length, ¼''; stout. Adherence to stone—weak.
Skin: Medium thick; tender; tenacious to flesh.
*Tendency to crack.*—None.
*Color.*—Cadmium Yellow, Plate 3, tinged pink on the sunny side.
*Down.*—Inconspicuous.
Flesh:
*Color.*—Deep Chrome, Plate 3. Surface of pit cavity, Deep Chrome, Plate 3.
*Amygdalin.*—Moderate.
*Texture.*—Firm; fine; melting.
*Fibres.*—Few; fine; tender.
*Ripens.*—Even; earliest at apex.
*Flavor.*—Mild; delicate.
*Aroma.*—Wanting.
*Eating quality.*—Best.

Stone: Free; parts from flesh smoothly. Fibres—none.
*Size.*—Medium; length 1''; breadth ⅞''.
*Thickness.*—⅜''.
*Form.*—Flat, winged.
*Base.*—Straight. Apex—rounded acute.
*Sides.*—Equal. Surface—smooth.
*Ridges.*—None.
*Pits.*—Elongated.
*Ventral edge.*—Thin, with slight wing.
*Dorsal edge.*—Full; no grooves; no ridges.
*Color of stone.*—Clay Color, Plate 29.
*Tendency to split.*—None.
Use: Market; dessert; culinary; canning.
Keeping quality: Good.
Resistance to:
*Insects.*—Good.
*Diseases.*—Good.
Shipping quality: Good.

I claim:

A new and distinct variety of apricot tree, characterized as to novelty by its vigor of growth; long blooming period with continuous and consistently prolific bearing year after year; large size fruit having sweet flavor even when picked green and allowed to ripen; high sugar content; substantially rectangular shape of the fruit; general high quality of the fruit and good keeping and shipping characteristics, substantially as shown and described.

DAVID A. MOORE.

No references cited.